United States Patent [19]

Hooven et al.

[11] Patent Number: 4,601,724
[45] Date of Patent: Jul. 22, 1986

[54] MANUFACTURE OF TUBING ASSEMBLY FOR DRAINAGE CATHETER

[75] Inventors: Michael D. Hooven; William S. Tremulis, both of Miami, Fla.

[73] Assignee: Cordis Corporation, Miami, Fla.

[21] Appl. No.: 614,633

[22] Filed: May 29, 1984

[51] Int. Cl.$^4$ .................. A61F 2/54; A61M 5/325; A61M 5/005

[52] U.S. Cl. .......................... 623/66; 604/8; 604/264; 604/266; 604/268

[58] Field of Search ............ 604/8, 264, 266, 268, 604/280; 623/66

[56] References Cited

U.S. PATENT DOCUMENTS

| | | | |
|---|---|---|---|
| 3,373,735 | 3/1968 | Gallagher | 604/280 X |
| 3,421,510 | 1/1969 | Kettenbach | 604/268 X |
| 3,426,759 | 4/1966 | Smith | 604/264 |
| 3,435,827 | 4/1969 | Ericson | 128/349 |
| 3,669,116 | 6/1972 | Heyer | 604/268 |
| 3,690,323 | 9/1972 | Wortman et al. | 128/350 R |
| 4,375,816 | 3/1983 | Labianca | 604/8 |
| 4,377,169 | 3/1983 | Banks | 604/8 |
| 4,391,276 | 7/1983 | Lazarus et al. | 604/266 |
| 4,398,910 | 8/1983 | Blake et al. | 604/266 X |

OTHER PUBLICATIONS

C. E. Garner et al., article, "Directed Ion Beam Sputter Etching of Polytetrafluoroethylene (Teflon) Using an Argon Ion Source", 1982, pp. 351–362.

Primary Examiner—Richard J. Apley
Assistant Examiner—Alan W. Cannon
Attorney, Agent, or Firm—Lockwood, Alex, FitzGibbon & Cummings

[57] ABSTRACT

A tubing assembly is provided which includes a length of elastomeric tubing over which is positioned and affixed a substantially shorter length of tubing having micro orifices ion sputtered therethrough. The tubing assembly is manufactured by a method that includes stretching the elastomeric tubing in association with the application of medical adhesive at an interface between the elastomeric tubing and the ion sputtered tubing, and relaxing the elastomeric tubing to provide an effective seal along the ends of the ion sputtered tubing. These tubing assemblies are particularly suitable for use as ventricular catheters within intracranial pressure relief systems.

25 Claims, 7 Drawing Figures

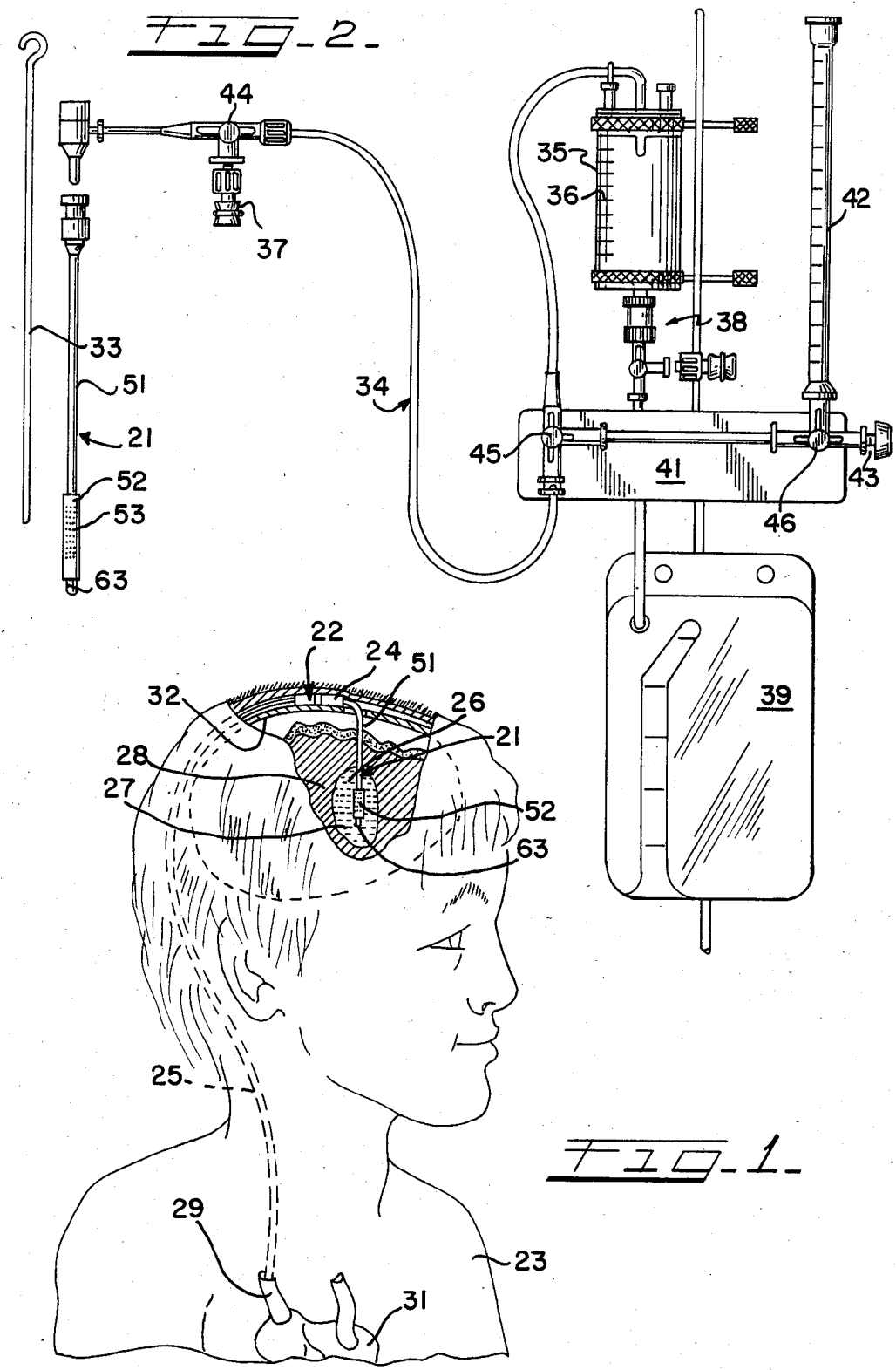

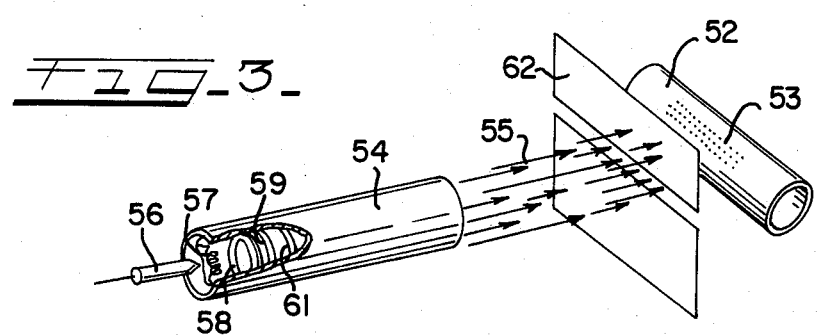
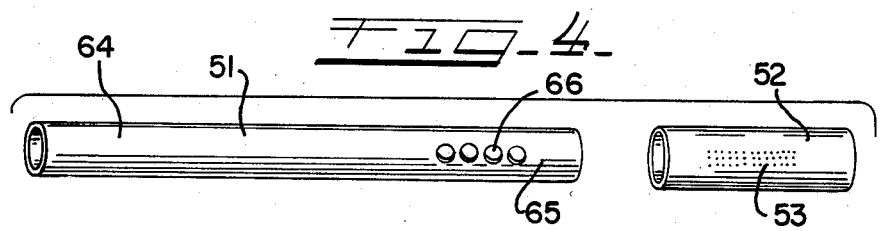
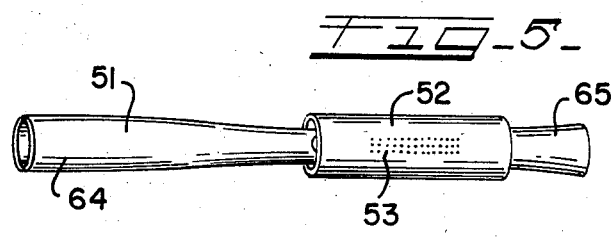
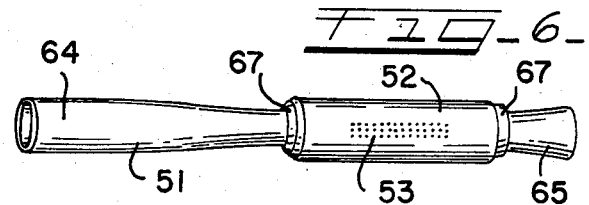
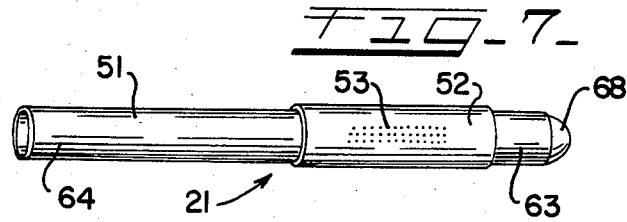

MANUFACTURE OF TUBING ASSEMBLY FOR DRAINAGE CATHETER

This invention generally relates to the making of tubing assemblies for catheters, more particularly to providing drainage catheters having extremely fine drainage inlets within a catheter tube that is flexible substantially throughout its length. In an important aspect of this invention, the extremely fine drainage inlets are ion sputtered into a relatively short tubing length which is stretchably affixed over a longer length of flexible tubing, such tubing assemblies being particularly suitable for ventricular catheters to gain access to and drain cerebrospinal fluid from a ventricle of the brain.

Systems for draining cerebrospinal fluid from the ventricle of the brain in order to control intracranial pressure, whether on a temporary or substantially permanent basis, have been known and used for a number of years. The more permanent types of these systems often include an implantable valve for allowing the passage of cerebrospinal fluid from a ventricle of the brain to a suitable drainage location in the body. Such implantable valves are actuatable by displacement of a diaphragm or the like therewithin in response to applied pressure differentials in order to regulate passage of cerebrospinal fluid from the ventricular spaces through a ventricular catheter and on to the drainage location. Similar types of ventricular catheters are included in temporarily implanted intracranial drainage, monitoring and/or injections systems which gain access to the ventricular spaces through a flexible ventricular catheter.

In these types of systems, flexibility of the ventricular catheter is important due to the delicate brain tissue within which it comes into contact. Additionally, it is important that the catheter orifices through which fluid flows should be extremely fine, preferably so small as to retard blockage thereof. It was heretofore known that a substantial decrease in high incidence of inlet blockage caused by the ingrowth of the choroid plexas, ventricular collapse over the catheter orifices, or hemorrhage, cellular and fibran debris, can be successfully controlled by forming the catheter orifices by ion sputtering techniques. However, procedures such as ion sputtering are not suitable for the flexible materials out of which these types of catheters are most advantageously manufactured, which materials are typically soft silicone rubber materials or other flexible tissue-compatible material. Instead, ion sputtering is particularly suitable for the formation of micro orifices within a relatively rigid material such as a fluoropolymer. Because of their rigidity, fluoropolymers are not well-suited for providing a single-stemmed catheter having a diameter that is typically required to achieve adequate flow therethrough in a ventricular catheter system. Heretofore, it has not been possible to provide a traditionally sized and shaped ventricular catheter having ion sputtered orifices which still possesses the flexibility that is extremely important for these types of catheters.

Such results have been attained by the present invention, by which the flexibility and non-traumatic properties of a material such as medical grade silicone rubber are combined with the receptiveness of a fluoropolymeric material to ion sputtered micro orifice formation, such combination being made possible by an advantageous utilization of the flexible and stretchable nature of the elastomeric tubing. The method and product produced thereby includes providing a length of elastomeric tubing having radially directed openings therethrough, ion sputtering radially directed orifices through a length of tubing that is substantially shorter than the elastomeric tubing, and inserting the shorter length of tubing over the elastomeric tubing length, typically in association with stretching the elastomeric tubing in order to thereby decrease its average diameter when extended. Thereafter, adhesive is applied along the edges of the shorter length of ion sputtered tubing, the elastomeric tubing being in a stretched condition, after which the elastomeric tubing is relaxed in order to encourage the adhesive to flow between and thus seal together the ion sputtered length of tubing and the length of elastomeric tubing.

It is accordingly a general object of the present invention to provide an improved catheter tube assembly.

Another object of this invention is to provide an improved method for manufacturing a tubular shaft having ion sputtered micro orifices while still providing an extremely flexible catheter shaft.

Another object of this invention is to provide an improved method and product produced thereby, which method includes taking advantage of the stretchability of an elastomeric tubing in combination with the formation of micro orifices by ion sputtering.

These and other objects of the present invention will be apparent from the following description of this invention, taken in conjunction with the accompanying drawings, wherein:

FIG. 1 is an illustration of the tubular assembly according to this invention utilized as a catheter within an intracranial pressure relief system that is shown implanted within a patient;

FIG. 2 is an elevational view illustrating the tubular assembly according to this invention incorporated into a temporarily implantable intracranial pressure monitoring and cerebrospinal fluid drainage sytem;

FIG. 3 is a schematic illustration, in perspective, depicting ion sputtering formation of micro orifices into a portion of the tubular assembly;

FIG. 4 is a perspective view illustrating the alignment of the components of the tubular assembly, prior to assembly thereof;

FIG. 5 is a perspective view illustrating initial assembly of one component of the tubular assembly onto the other;

FIG. 6 is a perspective view showing an intermediate stage in the manufacture of the tubular assembly; and FIG. 7 is a perspective view depicting a completed tubular assembly according to this invention suitable for use as a ventricular catheter.

A tubing assembly in accordance with this invention, generally designated as 21, is shown in FIG. 1 as a catheter component of an implantable cerebrospinal fluid pressure relief system, generally designated as 22. Such a system 22, which maintains a desired predetermined intracranial pressure in a patient 23, also includes a pressure relief valve 24 and a drain catheter 25. The cerebrospinal fluid pressure relief system 22 drains cerebrospinal fluid 26 from a ventricle 27 of the brain 28, the cerebrospinal fluid 14 passing through the pressure relief valve 24 and the drain catheter 25 for discharge into a selected location in the patient's body, such as an appropriate vein 29 to terminate within the right atrium of the heart 31 as illustrated. Other drainage locations, such as the peritoneal cavity, can be selected instead.

A typical pressure relief valve 24 in the pressure relief system 22 includes means for adjusting the differential pressure threshold at which the valve 24 opens so that the hydrocephalus pressure relief system 22 can be adjusted to suit the specific requirements of an individual patient. Various pressure relief valve assemblies are known. Ones that are particularly suitable to this aspect of the invention are those that are commercially available from Cordis Corporation. In such valves, the dimensions thereof are selected so as to be compatible with subcutaneous implantation of the valve 24 over the cranium 32.

Another suitable aspect of this invention is the inclusion of the tubing assembly 21 within an implantable pressure relief system such as that illustrated in FIG. 2, which is an intracranial pressure monitoring and cerebrospinal fluid drainage system. These types of systems are typically intended for a somewhat temporary implantation when compared to the implantation procedure for which the pressure relief system of FIG. 1 is intended. In the system of FIG. 2, the ventricular catheter or tubing assembly 21 is inserted into a ventricle of the brain in a manner similar to that illustrated in FIG. 1. However, the catheter 21 extends beyond the cranium 32 and the scalp of the patient.

In this regard, an introducer 33 is provided for guiding the catheter 21 into the ventricle in accordance with generally known medical procedures. A tubing assembly, generally designated as 34, is included for joining the catheter 21 with a drip chamber 35 having fluid measurement graduations 36 for collection and measurement of cerebrospinal fluid that is drained from the ventricle. Intracranial pressure may be measured through a monitoring port 37. Drip chamber 35 is part of a cerebrospinal fluid collection assembly 38 which may include a drainage bag 39. A monitoring assembly 41 may also be included to permit monitoring of cerebrospinal fluid pressure by either a monometer 42 or through a pressure transducer port 43 for communication with any one of a variety of electronic pressure monitoring devices. A plurality of four-way valves 44, 45 and 46 are preferably provided in the system of FIG. 2 in order to provide exceptional flexibility with regard to the various flow paths available within the system. Additional details of the pressure monitoring and fluid measuring and draining system illustrated in FIG. 2 are included in copending U.S. patent application Ser. No. 590,713, filed Mar. 16, 1984, the subject matter thereof being incorporated by reference hereinto.

With more particular reference to the catheter component or tubing assembly 21, such includes a length of elastomeric tubing 51 and a length of tubing 52 that includes ion sputtered orifices 53. The ion sputtered length of tubing is of a length shorter than that of the elastomeric tubing 51. Preparation of the ion sputtered tubing 52 is schematically illustrated in FIG. 3. An ion beam generator 54 of generally known construction provides an ion beam 55 from a source of gas such as argon or the like. Gas enters the ion beam generator 54 through a gas inlet 56, the ion beam generator 54 including an appropriate filament 57, anode 58, screen grid 59 and accelerator grid 61. Control of the ion beam 55 is typically facilitated by a shield or mask 62. A length of tubing that is especially suitable for the formation of ion sputtered micro orifices therein is positioned on the other side of the mask 62 in order to form the tubing 52 having the ion sputtered orifices 53.

With more particular reference to the tubing 52, it is typically not possible to form the ion sputtered orifices 53 in elastomeric materials such as those out of which the remainder of the tubing assembly 21 is made, this being the elastomeric tubing 51. Fluoropolymers are particularly receptive to ion sputtering techniques, although they are much less desirable for use as ventricular catheters than are elastomeric materials such as silicone rubber products and the like. Accordingly, the ion sputtered tubing 52 is of a relatively short length in order to minimize the surface area of the brain that is contacted by the ion sputtered non-elastomeric tubing 52, particularly during the implantation procedure.

In another important aspect of this invention, the ion sputtered non-elastomeric tubing 52 is spaced from the leading end 63 of the tubing assembly 21. The leading end 63 is made of a material that is elastomeric and exceptionally non-traumatic. Preferably, the leading end 63 is a continuous extension of the elastomeric tubing 51. The manufacture of the preferred tubing assembly 21 having these characteristics is illustrated in FIGS. 4 through 7.

In FIG. 4, a length of elastomeric tubing 51 is shown in an orientation for receiving the ion sputtered tubing 52 thereover. The preferred length of elastomeric tubing 51 includes a proximal length 64 and a distal length 65 for inclusion as a part of the leading end 63. At least one radially directed opening 66 is provided through the elastomeric tubing 51, thereby defining the proximal length 64 and the distal length 65 of the elastomeric tubing 51. Opening or openings 66 are positioned for substantially underlying relationship with the ion sputtered orifices 53 of the tubing 52 when the tubing 52 is assembled over the elastomeric tubing 51 in order to provide a fluid passageway from the outside surface of the ion sputtered orifices 53, through the opening(s) 66 and through the proximal length 64 of tubing 51 for passage to the rest of the cerebrospinal fluid drainage system or the like. While it is important that the ion sputtered orifices 53 be of an extremely fine size, there is no such requirement for the opening(s) 66.

Referring to FIG. 5, assembly of the ion sputtered tubing 52 over the elastomeric tubing 51 is facilitated by stretching the elastomeric tubing 51, which stretching reduces the outer diameter of the elastomeric tubing 51, whereupon the ion sputtered tubing can be assembled thereover. FIG. 6 illustrates an important aspect of this invention which insures the integrity of the assembly of the ion sputtered tubing 52 over the elastomeric tubing 51. A bead of medical adhesive 67 is applied along both ends of the ion sputtered tubing 52. Preferably the bead of medical adhesive 67 is applied around substantially the entire circumference of the ends of the ion sputtered tubing 52. Such beads of medical adhesive 67 are preferably applied while the elastomeric tubing 51 is stretched as illustrated in FIG. 6 in order to facilitate passage of the beads 67 between the elastomeric tubing 51 and the ion sputtered tubing 52 in the vicinity of the ends of the ion sputtered tubing 52.

Once the beads of medical adhesive 67 have become positioned between the elastomeric tubing 51 and the tubing 52, the elastomeric tubing 51 is relaxed as generally illustrated in FIG. 7, whereby the elastomeric tubing 51 is allowed to conform to its original dimensions, which assists in pulling the beads of medical adhesive 67 into the space between the elastomeric tubing 51 and the tubing 52, which space substantially closes between the orientation as illustrated in FIGS. 5 and 6 when the elastomeric tubing 51 was stretched and the closed orientation of FIG. 7. This results in the formation of a seal between the elastomeric tubing 51 and the ion sputtered tubing 52 at locations along the two ends of the ion sputtered tubing 52. Preferably, the distal length 65 of the elastomeric tubing 51 is closed by affixing a plug 68 thereto, which may be an adhesive, a molded tip or the like.

The internal diameter of the ion sputtered tubing 52 is substantially the same as or slightly less than the outer diameter of the elastomeric tubing 51 in its unstretched or relaxed state in order to insure that the assembled tubing assembly 21 exhibits a frictional fit between the ion sputtered tubing 52 and the elastomeric tubing 51. A suitable medical adhesive is one that readily bonds the components together at room temperature. Especially suitable medical adhesives include liquid silicone rubber or silicone elastomeric adhesives, or the like.

With more particular reference to the tubing 52, suitable fluoropolymers for making same include polytetrafluoroethylene resins including Teflon or other fluorine and/or chlorine containing fluoropolymers such as fluorinated ethylenepropylene. Materials of this type are particularly susceptible to being ion sputtered in order to form micro orifices 53 therewithin. Sizing of the micro orifices is important in order to substantially prevent undesirable tissue ingrowth while the tubing assembly 21 is implanted in vivo for extended periods of time. It is important that the passageway into the tubing assembly 21 through the ion sputtered micro orifices 53 not be blocked by tissue ingrowth or by other blockages such as having protein and cell fragments enter the orifices 53.

Such undesirable entry and ingrowth blockages can be accomplished by providing the orifices 53 as ion sputtered micro orifices each of which has a size less than that of such growing tissue, protein, cell fragments or the like. The ion sputtered micro orifices 53 will typically have a nominal diameter or a nominal opening width as small as on the order of about 5 microns up to a size at which ingrowth and blockage is substantially prevented in a patient, typically on the order of about 60 microns. A preferred size range is between about 10 and about 50 microns. By contrast, holes made by more conventional procedures in elastomeric tubing such as silicone rubber have a size on the order of about 400 microns.

It is to be appreciated that this invention can be embodied in various forms and therefore is to be construed and limited only by the scope of the appended claims.

We claim:

1. A method for manufacturing a tubing assembly, comprising:

providing a length of elastomeric tubing having a selected outer diameter, and forming at least one radially directed opening through the elastomeric tubing;

providing a length of non-elastomeric tubing having an internal diameter substantially equal to or less than said selected outer diameter of the elastomeric tubing;

ion sputtering radially directed micro orifices through the length of non-elastomeric tubing, said ion sputtered length of non-elastomeric tubing being shorter than said elastomeric tubing length, and said ion sputtered radially directed orifices each being smaller than said radially directed opening through the length of elastomeric tubing;

stretching said length of elastomeric tubing so as to reduce its said selected outer diameter, and inserting said ion sputtered length of tubing over said length of elastomeric tubing while same is at its reduced diameter, and simultaneously generally aligning said radially directed opening of the elastomeric tubing with said ion sputtered radially directed orifices of the non-elastomeric tubing;

applying adhesive along the radially directed axial edges of the ion sputtered length of non-elastomeric tubing while the elastomeric tubing length is stretched and at its reduced diameter; and relaxing said stretched elastomeric tubing length, whereby the elastomeric tubing substantially returns to its said selected outer diameter while the adhesive simultaneously flows between and adheres together with the ion sputtered length of non-elastomeric tubing and the elastomeric tubing in order to seal the non-elastomeric tubing over the elastomeric tubing at an orientation such that said opening through the elastomeric tubing is in substantially underlying relationship with said micro orifices of the non-elastomeric tubing.

2. The method according to claim 1, wherein said ion sputtering step includes passing a source of argon gas through an ion beam generator.

3. The method according to claim 1, wherein said ion sputtered length of tubing is a fluoropolymer tubing, and wherein said elastomeric tubing is a silicone rubber tubing.

4. The method according to claim 1, wherein said inserting step includes inserting said ion sputtered length of tubing such that the ion sputtered length of tubing is spaced from and defines a leading, distal length and a proximal length of said elastomeric tubing length.

5. The method according to claim 1, wherein said adhesive is a medical-grade adhesive and wherein said adhesive forms a seal between said ion sputtered tubing and said elastomeric length of tubing substantially at said axial edges of the ion sputtered length of tubing.

6. The method according to claim 1, further including closing the distal end of the elastomeric length of tubing by inserting an elastomeric plug thereinto.

7. The method according to claim 1, wherein said ion sputtered step forms micro orifices having a nominal opening width of between about 5 microns and up to about 60 microns and at which tissue ingrowth and blockage is substantially prevented.

8. The method according to claim 1, wherein said ion sputtered step forms micro orifices having a nominal opening width of between about 5 microns and about 60 microns.

9. A tubing assembly made by a process comprising:

providing a length of elastomeric tubing having a selected outer diameter, and forming at least one radially directed opening through the elastomeric tubing;

providing a length of non-elastomeric tubing having an internal diameter substantially equal to or less than said selected outer diameter of the elastomeric tubing;

ion sputtering radially directed micro orifices through the length of non-elastomeric tubing, said ion sputtered length of non-elastomeric tubing being shorter than said elastomeric tubing length, and said ion sputtered radially directed orifices each being smaller than said radially directed opening through the length of elastomeric tubing;

stretching said length of elastomeric tubing so as to reduce its said selected outer diameter, and inserting said ion sputtered length of tubing over said length of elastomeric tubing while same is at its reduced diameter, and simultaneously generally aligning said radially directed opening of the elastomeric tubing with said ion sputtered radially directed orifices of the non-elastomeric tubing;

applying adhesive along the radially directed axial edges of the ion sputtered length of non-elastomeric at its reduced diameter; and relaxing said stretched elastomeric tubing length, whereby the elastomeric tubing substantially returns to its said selected outer diameter while the adhesive simultaneously flows between and adheres together with the ion sputtered length of non-elastomeric tubing and the elastomeric tubing in order to seal the non-elastomeric tubing over the elastomeric tubing at an orientation such that said opening through the elastomeric tubing is in substantially underlying relationship with said micro orifices of the non-elastomeric tubing.

10. The tubing assembly according to claim 9, wherein said adhered together ion sputtered length of tubing and said elastomeric tubing form a ventricular catheter.

11. The tubing assembly according to claim 10, wherein said ion sputtered length of tubing is a fluropolymer tubing and wherein said elastomeric tubing is a silicone rubber tubing.

12. The tubing assembly according to claim 9, wherein said length of elastomeric tubing extends beyond both of said axial edges of the ion sputtered length of tubing.

13. The tubing assembly according to claim 12, wherein one of said elastomeric tubing extensions beyond an axial edge of the ion sputtered length of tubing has a plug closing same.

14. The tubing assembly according to claim 9, wherein said adhesive is a medical-grade adhesive and wherein said adhesive forms a seal between said ion sputtered tubing and said elastomeric length of tubing substantially at said axial edges of the ion sputtered length of tubing.

15. The tubing assembly according to claim 9, wherein said micro orifices have a nominal opening width of between about 5 microns and about 60 microns.

16. An implantable cerebrospinal fluid pressure relief system including a hydrocephalus pressure relief valve, draining means and a ventricular catheter, wherein the improvement comprises said ventricular catheter being made by a process including:

providing a length of elastomeric tubing having a selected outer diameter, and forming at least one radially directed opening through the elastomeric tubing;

providing a length of non-elastomeric tubing having an internal diameter substantially equal to or less than said selected outer diameter of the elastomeric tubing;

ion sputtering radially directed micro orifices through the length of non-elastomeric tubing, said ion sputtered length of non-elastomeric tubing being shorter than said elastomeric tubing length, and said ion sputtered radially directed orifices each being smaller than said radially directed opening through the length of elastomeric tubing;

stretching said length of elastomeric tubing so as to reduce its said selected outer diameter, and inserting said ion sputtered length of tubing over said length of elastomeric tubing while same is at its reduced diameter, and simultaneously generally aligning said radially directed opening of the elastomeric tubing with said ion sputtered radially directed orifices of the non-elastomeric tubing;

applying adhesive along the radially directed axial edges of the ion sputtered length of non-elastomeric tubing while the elastomeric tubing length is stretched and at its reduced diameter; and relaxing said stretched elastomeric tubing length, whereby the elastomeric tubing substantially returns to its said selected outer diameter while the adhesive simultaneously flows between and adheres together with the ion sputtered length of non-elastomeric tubing and the elastomeric tubing in order to seal the non-elastomeric tubing over the elastomeric tubing at an orientation such that said opening through the elastomeric tubing is in substantially underlying relationship with said micro orifices of the non-elastomeric tubing.

17. The implantable system according to claim 16, wherein said ion sputtered length of tubing is a fluoropolymer tubing, and wherein said elastomeric tubing is a silicone rubber tubing.

18. The implantable system according to claim 16, wherein said inserting step includes inserting said ion sputtered length of tubing such that the ion sputtered length of tubing is spaced from and defines a leading, distal length and a proximal length of said elastomeric tubing length.

19. The implantable system according to claim 16, wherein said adhesive is a medical-grade adhesive and wherein said adhesive forms a seal between said ion sputtered tubing and said elastomeric length of tubing substantially at said axial edges of the ion sputtered length of tubing.

20. The implantable system according to claim 16, wherein said ion sputtered step forms micro orifices having a nominal opening width of between about 5 microns and up to about 60 microns and at which tissue ingrowth and blockage is substantially prevented.

21. An intracranial pressure monitoring and cerebrospinal fluid drainage system including a ventricular catheter, a tubing assembly for joining the ventricular catheter to fluid measurement means and to pressure monitoring means, wherein the improvement comprises said ventricular catheter being made by a process including:

providing a length of elastomeric tubing having a selected outer diameter, and forming at least one radially directed opening through the elastomeric tubing;

providing a length of non-elastomeric tubing having an internal diameter substantially equal to or less than said selected outer diameter of the elastomeric tubing;

ion sputtering radially directed micro orifices through the length of non-elastomeric tubing, said ion sputtered length of non-elastomeric tubing being shorter than said elastomeric tubing length, and said ion sputtered radially directed orifices each being smaller than said radially directed opening through the length of elastomeric tubing;

stretching said length of elastomeric tubing so as to reduce its said selected outer diameter, and inserting said ion sputtered length of tubing over said length of elastomeric tubing while same is at its reduced diameter, and simultaneously generally aligning said radially directed opening of the elastomeric tubing with said ion sputtered radially directed orifices of the non-elastomeric tubing;

applying adhesive along the radially directed axial edges of the ion sputtered length of non-elastomeric tubing while the elastomeric tubing length is stretched and at its reduced diameter; and relaxing said stretched elastomeric tubing length, whereby the elastomeric tubing substantially returns to its said selected outer diameter while the adhesive simultaneously flows between and adheres together with the ion sputtered length of non-elastomeric tubing and the elastomeric tubing in order to seal the non-elastomeric tubing over the elastomeric tubing at an orientation such that said opening through the elastomeric tubing is in substantially underlying relationship with said micro orifices of the non-elastomeric tubing.

22. The system according to claim 21, wherein said ion sputtered length of tubing is a fluoropolymer tubing, and wherein said elastomeric tubing is a silicone rubber tubing.

23. The system according to claim 21, wherein said inserting step includes inserting said ion sputtered length of tubing such that the ion sputtered length of tubing is spaced from and defines a leading, distal length and a proximal length of said elastomeric tubing length.

24. The system according to claim 21, wherein said adhesive is a medical-grade adhesive and wherein said adhesive forms a seal between said ion sputtered tubing and said elastomeric length of tubing substantially at said axial edges of the ion sputtered length of tubing.

25. The system according to claim 21, wherein said ion sputtered step forms micro orifices having a nominal opening width of between about 5 microns and up to about 60 microns and at which tissue ingrowth and blockage is substantially prevented.

* * * * *

UNITED STATES PATENT AND TRADEMARK OFFICE
CERTIFICATE OF CORRECTION

PATENT NO. : 4,601,724
DATED : July 22, 1986
INVENTOR(S) : Michael D. Hooven and William S. Tremulis It is certified that error appears in the above—identified patent and that said Letters Patent is hereby corrected as shown below:

Column 4, line 51, "Preferably" should read --Preferably,--.
Column 5, line 28, "in vivo" should read --$\underline{in\ vivo}$--.
Column 7, line 11, insert --tubing while the elastomeric tubing length is stretched and-- before "at"; lines 28-29, "fluropolymer" should read --fluoropolymer--.

Signed and Sealed this

Twenty-eighth Day of October, 1986

[SEAL]

Attest:

DONALD J. QUIGG

*Attesting Officer*   *Commissioner of Patents and Trademarks*